United States Patent [19]

Voege et al.

[11] Patent Number: 4,628,054
[45] Date of Patent: Dec. 9, 1986

[54] STABILIZING QUINOXALINE DI-N-OXIDES AGAINST LIGHT DEGRADATION

[75] Inventors: Herbert Voege, Leverkusen; Hans U. Sieveking, Cologne, both of Fed. Rep. of Germany

[73] Assignee: Bayer Aktiengesellschaft, Leverkusen, Fed. Rep. of Germany

[21] Appl. No.: 767,012

[22] Filed: Aug. 19, 1985

Related U.S. Application Data

[63] Continuation of Ser. No. 520,100, Apr. 4, 1983, abandoned.

[30] Foreign Application Priority Data

Aug. 14, 1982 [DE] Fed. Rep. of Germany ....... 3230273

[51] Int. Cl.⁴ ................. C07D 241/44; C07D 413/06; C07D 403/06; A61K 31/495
[52] U.S. Cl. .................................. 514/234; 514/249; 544/116; 544/355
[58] Field of Search ............... 544/353, 354, 116, 355; 514/234, 249

[56] References Cited

U.S. PATENT DOCUMENTS

| | | | |
|---|---|---|---|
| 3,726,630 | 12/1975 | Van den Horte | 544/353 |
| 3,862,951 | 1/1975 | Gottwald et al. | 544/353 |
| 3,908,008 | 9/1975 | Ley et al. | 544/353 |
| 4,171,355 | 10/1979 | Stubbs | 424/174 |
| 4,228,151 | 10/1980 | Lang | 544/353 |

FOREIGN PATENT DOCUMENTS

| | | |
|---|---|---|
| 1954226 | 7/1970 | Fed. Rep. of Germany. |
| 2147545 | 4/1972 | Fed. Rep. of Germany. |
| 2615646 | 10/1976 | Fed. Rep. of Germany. |

*Primary Examiner*—Mark L. Berch
*Attorney, Agent, or Firm*—Sprung Horn Kramer & Woods

[57] ABSTRACT

Quinoxaline di-N-oxides used in animal feeds, such as olaquindox, are stabilized against light degradation by substances which absorb light within the wavelength range from 200 to 450 nm, such as quinolines, isoxanthenones, azo dyestuffs, polyenes and/or flavones.

11 Claims, No Drawings

STABILIZING QUINOXALINE DI-N-OXIDES AGAINST LIGHT DEGRADATION

This is a continuation, of application Ser. No. 520,100, filed Apr. 4, 1983, now pending.

The invention relates to quinoxaline di-N-oxides formulations containing chemical substances which absorb light within the wavelength range from 200 to 450 nm.

Quinoxaline di-N-oxides having an antibiotic action are chiefly used as growth promoters or as medicaments in animal medicine. In rearing poultry it is customary to administer medicaments to the birds via the drinking water, and the same is also true in the case of pigs and others. A solution of the active compound in water is advantageous for this purpose, because this ensures a homogenous distribution, and, it is not possible for particles of active compound to be deposited in the drink and to be lost or to block up jets.

It is an object of the invention to increase the effectiveness of the administered quinoxaline di-N-oxides.

It has been found that freshly administered solutions of quinoxaline di-N-oxides have a greater effect than solutions which are made, stored and later administered. Our investigations have revealed this is due to degradation of the quinoxaline di-N-oxide upon standing, particularly when exposed to light. Depending on the intensity of the light and the concentration of the active compound, more than half the active compound is destroyed under the influence of light in less than 1 hour.

The invention therefore increases the effectiveness of the quinoxaline di-N-oxides by stabilizing them against light degradation by admixing them with chemical substances which absorb light. within the wavelength range from 200 ro 450 nm. Preferred quinoxaline di-N-oxides formulations are those containing chemical substances which absorb light within the wavelength range from 200 to 450 nm and increase the proportion of quinoxaline di-N-oxide remaining by at least 50%, determined on an aqueous solution containing 100 ppm of quinoxaline di-N-oxide and 100 ppm of absorbing substance, when irradiated for 1 hour with UV light of wavelength 366 nm (Desaga lamp for thin layer chromatography plates at a distance of 15 cm).

The invention also relates preferentially to aqueous quinoxaline di-N-oxide solutions containing chemical substances having absorption ranges from 300 to 400 nm.

The quinoxaline di-N-oxides employed are those of the formula I

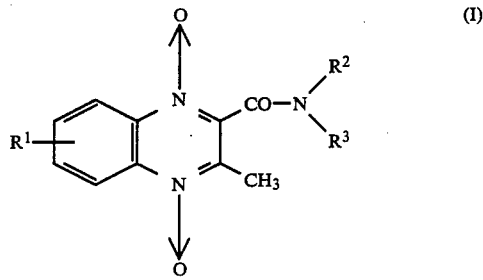

in which
$R^1$ represents a hydrogen or chlorine atom or a lower alkyl group or lower alkoxy group,
$R^2$ represents a straight-chain or branched alkyl radical which has 1 to 6 carbon atoms and is optionally substituted by a hydroxyl, lower alkoxy, lower alkylamino or lower dialkylamino group, or represents the group

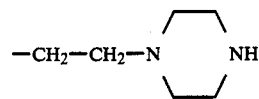

and
$R^3$ represents a hydrogen atom or a straightchain or branched alkyl radical which has 1 to 6 carbon atoms and is optionally substituted by a hydroxyl, lower alkoxy, lower alkylamino or lower dialkylamino group, and in which $R^2$ and $R^3$, together with the amide nitrogen atom to which they are attached, can form a pyrrolidino, piperidino, morpholino or piperazino radical; it being possible for the latter to be substituted in the 4-position by a lower alkyl radical which can, in turn, be substituted by a hydroxyl group; and lower alkyl or alkoxy groups being understood in all cases to mean groups having 1 to 4 carbon atoms.

It is particularly preferable for the preparations according to the invention to contain the quinoxaline di-N-oxide of the formula

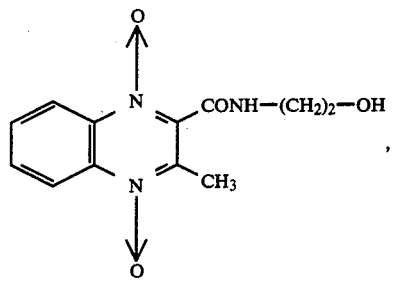

which is also known under the name olaquindox and which is of importance in animal nutrition.

A pronounced stabilization to light is achieved in accordance with the invention using substances which absorb light within the extinction range from 200 to 450 nm.

The class of chemical substances to which these substances belong is not important in this respect. Thus substances belonging to the class comprising the quinoline derivatives can have a protective action for the active compounds mentioned here, for example N,N'-bis-[1-methylquinolinium-6-methylsulphate](quiuronium sulphate), substances belonging to the class comprising the isoxanthenones, such as fluorescein, which is known, azo dyestuffs, such as, for example, tartrazine, and polyenes, such as, for example, the annatto dyestuffs; flavones, such as rutin, which occurs naturally, also protect the soluble quinoxaline di-N-oxides against degradation by light.

The light stabilization depends on the amount of substance added. This is normally 0.1 to 10 times the amount of quinoxaline di-N-oxide, but the substance should preferably be effective in an amount smaller or similar to that of the quinoxaline di-N-oxide used.

Since the active compounds are used within a range from 25 ppm to 500 ppm, light stabilization results when the active compounds are employed within this quantity range.

The substances to be protected are simply mixed with the active compounds or with the existing formulations, for example water-soluble powders or suspensions. They can, of course, also be added separately to the water.

The examples which follow serve to illustrate the invention.

MATERIAL AND METHODS

1. Irradiation conditions

Aqueous solutions containing 100 ppm of olaquindox were irradiated under standardized conditions: This was effected by exposing 100 ml of solution in open crystallization dishes ($\phi$:7.5 cm; layer thickness: 2.2 cm) to the source of light (distance 15 cm).

2. Source and duration of radiation (a) UV light (long-wave, 366 nm) from a Desaga lamp (for thin layer chromatography plates), distance from sample:
10 cm, duration of radiation: 1 hr.

3. Concentration of additives
100 ppm
10 ppm

4. Analytical conditions

The content of active compound was determined by means of thin layer chromatography/UV; in general it was possible to separate the additives using chloroform/methanol (10+1) as the mobile phase. In the case of fluorescein, ethyl acetate/acetone/ethanol/diethylamine (50+40+10+5) was used. When the degradation of active compound was very great, the content of active compound was estimated visually (comparison of spots on a thin layer chromatographic plate), at concentrations of 15% of the theoretical value, the eluate was subjected to analysis.

The results shown in the following table were obtained.

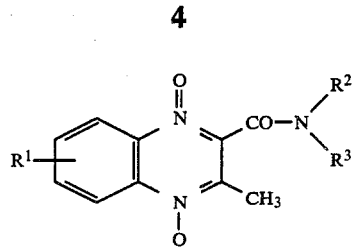

wherein
R$^1$ represents a hydrogen or chlorine atom or a lower alkyl group of lower alkoxy group,
R$^2$ represents a straight-chain or branched alkyl radical which has 1 to 6 carbon atoms and is optionally substituted by a hydroxyl, lower alkoxy, lower alkylamino or lower dialkylamino group, or represents the group

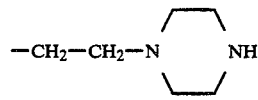

and
R$^3$ represents a hydrogen atom or a straightchain or branched alkyl radical which has 1 to 6 carbon atoms and is optionally substituted by a hydroxyl, lower alkoxy, lower alkylamino or lower dialkylamino group, or in which R$^2$ and R$^3$, together with the amide nitrogen atom to which they are attached, can form a pyrrolidino, piperidino, morpholino or piperazino radical; it being possible for the latter to be substituted in the 4-position by a lower alkyl radical; lower alkyl or alkoxy groups being understood in all cases to mean groups having 1 to 4 carbon atoms,
and a light stabilizing amount of a substance which absorbs light within the wavelength range from 200 to 450 nm and selected from the group consisting of quiuronium sulphate, tartrazine XX, rutin, sodium salt of fluorescein, water-soluble bixin and sodium alizarin

TABLE

| Light stabilizing additive | Concentration (ppm) | UV light (366) 1 hr. olaquindox content (% of initial 100 ppm) |
|---|---|---|
| Olaquindox without light stabilization | — | 15 |
| Quiuronium sulphate (generic name) | 100 | 39 |
| Tartrazine XX (Colour Index 2956, 19, 140) | 100 | 29 |
| 3,5,7,3',4'-pentahydroxyflavone-3-rutinoside (= rutin = Vitamin P), water-soluble | 100 | 30 |
| Sodium salt of fluorescein | 100 | 34 |
| Water-soluble bixin (= norbixin, vegetable dyestuff of the carotinoid type) | 100 | 28 |
| Sodium alizarin sulphonate | 100 | 33 |
| o-Aminobenzoic acid | 100 | 25 |
| Sodium 2-phenylbenzimidazole-5-sulphonate | 100 | 27 |

It will be understood that the specification and examples are illustrative but not limitative of the present invention and that other embodiments within the spirit and scope of the invention will suggest themselves to those skilled in the art.

What is claimed is:

1. A composition consisting essentially of a quinoxaline di-N-oxide of the formula sulphonate.

2. A composition according to claim 1, in which the light absorber is quiuronium sulphate, rutin or sodium alizarin sulphonate.

3. A composition according to claim 1, wherein the light absorber absorbs light within the wavelength range from 300 to 400 nm.

4. A composition according to claim 1, in which the light absorber is tartrazine XX.

5. A composition according to claim 1, wherein the light absorber is present in about 0.1 to 10 times the weight of the di-N-oxide.

6. An aqueous solution of a composition according to claim 1, wherein the light absorber absorbs light within the wavelength range from 300 to 400 nm and is present in about 0.1 to 10 times the weight of the quinoxaline di-N-oxide which is olaquindox.

7. A composition according to claim 1, wherein the quinoxaline di-N-oxide is of the formula

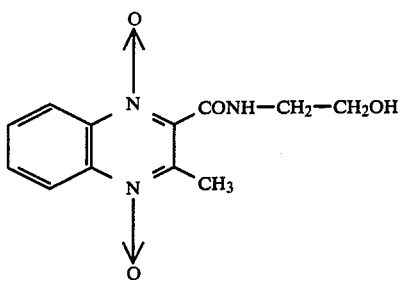

8. A composition according to claim 1, in the form of an aqueous solution.

9. In the administration of a quinoxaline di-N-oxide of the formula

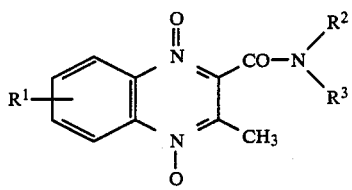

wherein
$R^1$ represents a hydrogen or chlorine atom or a lower alkyl group or lower alkoxy group, $R^2$ represents a straight-chain or branched alkyl radical which has 1 to 6 carbon atoms and is optionally substituted by a hydroxyl, lower alkoxy, lower alkylamino or lower dialkylamino group, or represents the group

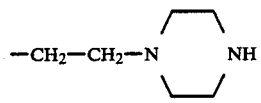

and
$R^3$ represents a hydrogen atom or a straightchain or branched alkyl radical which has 1 to 6 carbon atoms and is optionally substituted by a hydroxyl, lower alkoxy, lower alkylamino or lower dialkylamino group, or in which $R^2$ and $R^3$, together with the amide nitrogen atom to which they are attached, can form a pyrrolidino, piperidino, morpholino or piperazino radical; it being possible for the latter to be substituted in the 4-position by a lower alkyl radical; lower alkyl or alkoxy groups being understood in all cases to mean groups having 1 to 4 carbon atoms, to an animal by dissolving the quinozaline di-N-oxide in water and then adding the solution to the animal's drinking water or food product, the improvement which comprises adding to the solution a substance which absorbs light within the wavelength range from 200 to 450 nm and selected from the group consisting of quiuronium sulphate, tartrazine XX, rutin, sodium salt of fluorescein, water-soluble bixin and sodium alizarin sulphonate.

10. A process according to claim 9, in which the light absorber is quiuronium sulphate, rutin or sodium alizarin sulphonate.

11. A process according to claim 9 in which the light absorber is tetrazine XX.

* * * * *